US008685616B2

(12) United States Patent
Gonsalves et al.

(10) Patent No.: US 8,685,616 B2
(45) Date of Patent: Apr. 1, 2014

(54) PHOTOACID GENERATORS AND LITHOGRAPHIC RESISTS COMPRISING THE SAME

(75) Inventors: Kenneth E. Gonsalves, Concord, NC (US); Mingxing Wang, Matthews, NC (US)

(73) Assignee: University Of North Carolina At Charlotte, Charlotte, NC (US)

( * ) Notice: Subject to any disclaimer, the term of this patent is extended or adjusted under 35 U.S.C. 154(b) by 189 days.

(21) Appl. No.: 12/997,132

(22) PCT Filed: Jun. 10, 2009

(86) PCT No.: PCT/US2009/046957
§ 371 (c)(1),
(2), (4) Date: Feb. 25, 2011

(87) PCT Pub. No.: WO2009/152276
PCT Pub. Date: Dec. 17, 2009

(65) Prior Publication Data
US 2011/0159431 A1 Jun. 30, 2011

Related U.S. Application Data

(60) Provisional application No. 61/112,546, filed on Nov. 7, 2008, provisional application No. 61/060,166, filed on Jun. 10, 2008.

(51) Int. Cl.
*G03F 7/004* (2006.01)
*C07C 303/38* (2006.01)
*G03F 7/039* (2006.01)

(52) U.S. Cl.
CPC .............. *G03F 7/0045* (2013.01); *G03F 7/039* (2013.01); *C07C 303/38* (2013.01); *Y10S 430/106* (2013.01); *Y10S 430/12* (2013.01); *Y10S 430/122* (2013.01); *Y10S 430/123* (2013.01)
USPC ........ 430/270.1; 430/905; 430/919; 430/921; 430/922; 564/82

(58) Field of Classification Search
CPC ....... G03F 7/039; G03F 7/045; G03F 7/0045; C07C 303/38
USPC .......... 430/270.1, 905, 919, 921, 922; 564/82
See application file for complete search history.

(56) References Cited

U.S. PATENT DOCUMENTS

| | | | |
|---|---|---|---|
| 3,849,137 A | 11/1974 | Barzynski et al. | |
| 4,225,664 A | 9/1980 | Moran et al. | |
| 4,717,513 A | 1/1988 | Lewis et al. | |
| 5,130,392 A | 7/1992 | Schwalm et al. | |
| 5,348,656 A | 9/1994 | Podszun et al. | |
| 5,459,021 A | 10/1995 | Ito et al. | |
| 5,750,680 A | 5/1998 | Kim et al. | |
| 5,780,201 A | 7/1998 | Sabnis et al. | |
| 5,945,250 A | 8/1999 | Aoai et al. | |
| 5,965,325 A | 10/1999 | Matsuo et al. | |
| 6,017,677 A | 1/2000 | Maemoto et al. | |
| 6,051,678 A | 4/2000 | Kim et al. | |
| 6,129,928 A | 10/2000 | Sarangapani et al. | |
| 6,132,644 A * | 10/2000 | Angelopoulos et al. | ...... 252/500 |
| 6,232,034 B1 | 5/2001 | Kasai et al. | |
| 6,238,541 B1 | 5/2001 | Sasaki et al. | |
| 6,280,911 B1 | 8/2001 | Trefonas, III | |
| 6,306,556 B1 | 10/2001 | Matsuo et al. | |
| 6,391,471 B1 | 5/2002 | Hiraoka et al. | |
| 6,420,084 B1 | 7/2002 | Angelopoulos et al. | |
| 6,468,717 B2 | 10/2002 | Kita et al. | |
| 6,468,725 B2 | 10/2002 | Takamuki | |
| 6,479,210 B2 | 11/2002 | Kinoshita et al. | |
| 6,492,086 B1 | 12/2002 | Barclay et al. | |
| 6,512,081 B1 | 1/2003 | Rizzardo et al. | |
| 6,517,958 B1 | 2/2003 | Sellinger et al. | |
| 6,696,148 B1 | 2/2004 | Seino et al. | |
| 6,716,919 B2 | 4/2004 | Lichtenhan et al. | |
| 6,869,748 B2 | 3/2005 | Takeda et al. | |
| 6,884,562 B1 | 4/2005 | Schadt, III et al. | |
| 7,008,749 B2 | 3/2006 | Gonsalves | |
| 7,049,044 B2 | 5/2006 | Gonsalves et al. | |
| 7,776,505 B2 | 8/2010 | Gonsalves | |
| 7,833,690 B2 | 11/2010 | Gonsalves et al. | |
| 2002/0015913 A1 | 2/2002 | Uetani et al. | |
| 2002/0051928 A1 | 5/2002 | Zampini | |
| 2002/0081523 A1 | 6/2002 | Uetani et al. | |
| 2002/0147259 A1 | 10/2002 | Namba et al. | |
| 2002/0182541 A1 | 12/2002 | Gonsalves | |

(Continued)

FOREIGN PATENT DOCUMENTS

EP 0473547 3/1992
EP 1736824 A1 3/1992

(Continued)

OTHER PUBLICATIONS

Ahn et al., "photoacid generating polymers based on sulfonyloxymaleimides and application as single-component resists", J. Polym. Sci. Polym. Chem. Ed. 1996, 34(2):183.
Boeckh et al, "Copolymers Prepared by Ring-Opening Polymerization of Cyclic Ketens with Unsaturated Anhydrides", Chem. Abstract of DE 3927811A1, 1991.
Bowden et al., "Electronic and Photonic Applications of Polymers", ACS Series 218, 1988.
Brainard, "Resists for next generation lighography", Microelectronic Engineering, 2002, article in press, vols. 61-62, pp. 707-715.
Bruining et al., "New biodegradable networks of poly(N-vinylpyrrolidinone) designed for controlled nonburst degradation in the vitreous body" J. Biomed. Mater. Res., 1999, 47 (2), 189-197.
Canning, "Next Generation Lithography: When, Why and at what cost?" Microelectronic Engineering, 2002, vols. 61-62, p. 7.
Curtis et al., "Topographical control of cells", Biomaterials, 1997, 18(24), 1573-1583.
Curtis et al., "Reactions of cells to topography", J. Biomater. Sci., 1998, 9 (12), 1313-1329.

(Continued)

*Primary Examiner* — John Chu
(74) *Attorney, Agent, or Firm* — J. Clinton Wimbish; Smith Moore Leatherwood LLP

(57) ABSTRACT

The present invention provides photoacid generators for use in chemically amplified resists and lithographic processes using the same.

5 Claims, 21 Drawing Sheets

(56) References Cited

U.S. PATENT DOCUMENTS

| | | |
|---|---|---|
| 2003/0146418 A1 | 8/2003 | Chacko |
| 2003/0194634 A1 | 10/2003 | Nagai et al. |
| 2004/0029037 A1 | 2/2004 | Kamabuchi et al. |
| 2004/0166432 A1 | 8/2004 | Ohsawa et al. |
| 2004/0224259 A1 | 11/2004 | Anzures et al. |
| 2004/0229161 A1 | 11/2004 | Yasunami et al. |
| 2004/0248039 A1 | 12/2004 | Sounik et al. |
| 2005/0014098 A1 | 1/2005 | Gonsalves et al. |
| 2005/0208419 A1 | 9/2005 | Inabe et al. |
| 2005/0244452 A1 | 11/2005 | Gonsalves |
| 2006/0024610 A1 | 2/2006 | Padmanaban et al. |
| 2006/0121390 A1 | 6/2006 | Gonsalves |
| 2008/0081292 A1* | 4/2008 | Tsuchihashi et al. ...... 430/287.1 |

FOREIGN PATENT DOCUMENTS

| | | |
|---|---|---|
| EP | 1906248 A | 4/2008 |
| JP | 05086133 | 4/1993 |
| JP | 06228086 | 8/1994 |
| JP | 10221852 | 8/1998 |
| JP | 11167199 | 6/1999 |
| JP | 2000-334881 | 12/2000 |
| JP | 2003-322972 | 11/2003 |
| JP | 2006-178317 | 7/2006 |
| WO | 0174411 | 10/2001 |
| WO | 02097533 A1 | 12/2002 |
| WO | 2005/109102 | 11/2005 |
| WO | 2008/153109 | 12/2008 |

OTHER PUBLICATIONS

Kim et al., "Novel protein kinase C inhibitors: a-terthiophene derivatives", Bioorganic and Medicinal Chemistry Letter, 1998, 8 (10), 2695-2698.

Ely et al., "Common molecular scaffold for two unrelated RGD molecules", Protein Engineering, 1995, 8 (8), 823-827.

Garnier et al., "Toward intelligent polymers: DNA sensors based on oligonucleotide-functionalized polyprroles", Synth. Met., 1999, 100 (1), 89-94.

Godillot et al., "Direct chemical functionalization of as-grown electroactive polyprrole film containing leaving groups" Synth Met, 1996, 83 (2), 117-123.

Gonsalves et al., "Organic-inorganic Nanocomposites: Unique Resists for Nanolithography", Adv. Mater., 2001, 13 (10), 703-714.

Gonsalves et al., "High Resolution Resists for Next Generation Lithography: The Nanocomposite Approach", Materials Research Society Symposium Proceedings, (2000 Fall Meeting Proceedings Nov. 27-Dec. 1, 2000), vol. 636, pp. D6.5.1-D6.5.11.

Gonsalves et al, "Combinatorial approach for the synthesis of terpolymers and their nevel application as very-high-contrast resists for x-ray nanolithography", J. Vac. Sci, Technol. B., 2000, 18 (1), 325-327.

Gonsalves et al., "Synthesis and Proeprties of Degradable Polyamides and Related Polymers", TRIP, 1996, 4 (1), 25.

Haddad et al., "Hybrid Organic-Inorganic Thermoplastics: Styryl-Based Polyhedral Oligomeric Sisesquioxane Polymers", Macromolecules, 1996, 29, 7302-7304.

He et al., Synthesis, Characterization, and Preliminary Biological Study of Poly,(3-(tert-butoxycarbonyl)-N-vinyl-2-pyrrolidone), Biomacromolecules, 2003, 4, 75-79.

He et al., "Lithography Application of a Novel Photoresist for Patterning of Cells", Biomaterials, 2004, 25, 2055.

Hu et al., "Nanocomposite resists for electron beam nanolithography", Microelectronic Engineering, 2001, 56, 289-294.

Irvine et al., "Nanoscale clustering of RGD peptides at surfaces using Comb polymers", Biomacromolecules, 2001, 2 (1), 85-94.

Ito et al., "Influence of acid generator structure on T-top formation in high-temperature bake processes for envirnonmental stabilization", Proc, SPIE, 1995, 2438, 53-60.

Ito et al., "Annealing Concept for the Design of Environmentally Stable Chemical Amplification Resists", J. Photopolym. Sci. Technol., 1995, 8, 505-518.

Jin et al., "Functionalized copolymers and their composites with polylactide and hydroxyapatite", J. Mater. Sci. Med., 1999, 10(6), 363-368.

Jin et al., "Synthesis and Characterization of Functionalized Poly(c-caprolactone) Copolymers by Free-Radical Polymerization", Macromolecules, 1998, 31(4), 1010-1015.

Kam et al., "Selective adhesion of astrocytes to surfaces modified with immobilized peptides", Biomaterials, 2002, 23 (2), 511-515.

Kirby et al. "Nonlinear, three-dimensional finite-element model of skin biomechanics", J. Otolaryngol., 1998, 27(3), 153-160.

Korenkov et al., "Biomechanical and morphological types of the linea alba and its possible role in the pathogenesis of midline incisional hernia", Eur, J. Surg., 2001, 167 (12), 909-914.

Leboucher-Durand et al., "4-Carboxy-2-Oxetanone as a New Chiral Precursor in the Preparation of Functionalized Racemic or Optically Active Poly(malic acid) Derivatives", Chem Abstract of Polymer Bulletin (Berlin), 1996, 36 (1).

Lipton et al., "A biomechanical study of the aponeurotic inguinal hernia repair", J. Am. Coll. Surg., 1994, 178 (6), 595-599.

Maganaris, C.N., "Tensile properties of in vivo human tendinous tissue", J. Biomech., 2002, 35 (8), 1019-1027.

Matyjaszewski et al., "Synthesis of Functional Polymers by Aton Transfer Radical Polymerization", ACS Symposium Series 704, Patil et al. (eds.), 1997, 16-27.

Merhari et al., "Nanocomposite resist systems for next generation lithography", Microelectronic Engineering, 2002, vol. 63, pp. 391-403.

Mooney et al., "Long-term engraftment of hepatocytes transplanted on biodegradable polymer sponges", J. Biomed. Mater. Res., 1997, 37 (3), 413-420.

Moreau, W. M., "Semiconductor Lithography: Principles, Practices, and Materials", Plenum, New York, 1987.

Mudera et al., "Molecular responses of human dermal fibroblasts to dual cues: contact guidance and mechanical load", Cell Motil. Cytoskeleton, 2000, 45, 1-9.

Pan et al., "Synthesis and polymerization of 2-butyl-7-methylene-1,4,6-trioxaspiro(4,4) nonane", Polym. Sci. Chem. Ed., 1988, 26 (20), 2737.

Castiglione et al., "Synthesis and preliminary biological investigations of O-sulphated demorphin", Int. J. Peptide Protein Res., 1983, 21 (5), 471-474.

Pierschbacher, MD et al., "Cell attachment activity of fibronectin can be duplicated by small synthetic fragments of the molecule", Nature, 1984, 309 (5963), 30-33.

Pyun et al., Chemical Abstract for "Synthesis of Organic/Inorganic Hybrid Materials from Polysiloxane Precursors Using Atom Transfer Radical Polymerization", Polymer Preprints, 1999, 40 (2), 454-455.

Rajnicek, "Guidance of CNS growth cones by substratum grooves and ridges: effects of inhibitors of the cytoskeleton, calcium channels and signal transduction pathways", J. Cell Sci., 1997, 110 (23), 2915-2924.

Saito, S., "A new positive electron-beam resist material composed of catechol derivatives", Microelectronic Engineering, 2002, vols. 61-62, pp. 777-781.

Saltzman, W.M., "Cell interactions with polymers": in Principles of Tissue Engineering, Lanza, P.P. et al. (eds.), Academic Press, New York, 2000, 221-235.

Shastri et al., "Application of Conductive Polymers in Bone Regeneration", Mater. Res. Soc. Symp. Proc., 1999, 550, 215-219.

Singhvi et al., "Effects of substratum morphology on cell physiology", Biotechnol. Bioeng., 1994, 43 (8), 764-771.

Stingl et al., "Morphology and some biomechanical properties of human liver and spleen", Surg. Radiol. Anat., 2002, 24 (5), 285-289.

Storch et al., "A 28-day study of the effect of Coated VICRYL Plus Antibacterial Suture (coated polyglactin 910 suture with triciosan) on wound healing in guinea pig linear incisional skin wounds", Surg. Infect. (Larchmt.), 2002, 3 (1), 89-98.

Thackeray et al., "Developmentally regulated alternative splicing generates a complex array of *Drosophila* para sodium channel isoforms", J. of Neuroscience, 1994, 14 (5 pt 1), 2569-2578.

Von Recum et al., "Surface Roughness, Porosity, and Texture as Modifiers of Cellular Adhesion", Tissue Eng., 1996, 2,241.

(56) References Cited

OTHER PUBLICATIONS

Walboomers et al., "Growth behaviour of fibroblasts on microgrooved polystyrene", Biomaterials, 1998, 19 (20), 1861-1868.
Walboomers et al., "Attachment of fibroblasts on smooth and microgrooved polystyrene", J. Biomed. Mater. Res., 1999, 46 (2), 212-220.
Wallraff et al., "Lithographic Imaging Techniques for the Formation of Nanscopic Features", Chem. Rev., 1999, 99 (7), 1801-1822.
Wu et al., "Chemical Abstract for Polymer-Inorganic High Contrast and High Sensitivity Resists for Nanolithography", Materials Research Society Symposium Proceedings, 2000, 584, 121-128.
Wu et al., "Incorporation of polyhedrahl oligosilsesquioxane in chemically amplified resists to improve their reactive ion etching resistance", J. Vac. Sci. Technol. B, 2001, 19 (3), 851-855.
Wu et al., "Synthesis and Characterization of Radiation-sensitive Polymers and Their Application in Lithography", Ph. D. dissertation, University of Connecticut, Apr. 2001.
Wu et al., "Preparation of a Photoacid Gerating Monomer and its Application in Lithography", Advanced Functional Materials, 2001, 11 (4), 271-276.
Wu et al., "A Novel Single-Component Negative Resist for DUV and Electron Beam Lithography", Advanced Functional Materials, 2001, 13 (3), 195-197 111.
Yamaoka et al., "Synthesis and properties of malic acid-containing functional polymers", Inter. J. Biological Macromolecules, 1999, 25 (1-3), 265-271.
Yuan et al., "Block copolymerization of 5,6-benzo-2-methylene-1,3-dioxepane with conventional vinyl monomers by ATRP method", European Polymer J., 2002 38 (8), 1565-1571, 2069-2076.
Kim et al., "A novel water developable photoresist for deep UV lithography", Eur. Polym. J., 1997, 33(8), 1239-1243.
Kim et al., "Copolymers of camphoosulfonyloxymalemide . . . ", Polymer Bull., 1997, 39, 423-430.
Wu et al., "Novel CA resists with photoacid generator in polymer chain", Proceed. of SPIE, 2001, 4345, 521-527.
Nicolau et al., Blosensors & Bioelectronics, 1999, 14, 317-325.
Sang-Wook Park et al., "A novel photoresist based on polymeric amplifiers", Chemistry Letters, 29 (9), 2000, 1036-1037.
International Technology Roadmap for Semiconductors 2005 Edition Lithography, 29 pages.
Harriott, L. R., Next generation lithography, Mater. Sci. in Semiconductor Processing, 1, 1998, 93-97.
Broers, A. N. , IBM J. Res. Develop. 32, No. 4, 502-513 (1988).
Ishii et al., J. Vac. Sci. Technol. B, 1997, 15, No. 6, 2570-2574.
Chu et al., Plasma-surface modification biomaterials, Mater. Sci. Eng. R. 2002, 36, 143-206.
Svorcik et al., J. Mater. Sci.: Mater. Med., 2000, 11, 655-660.
Dalton et al., Bio Techniques, 1996, 21, 298-303.
Webster et al., Scripta Mater., 2001, 44(8-9), 1639-1642.
Thackeray et al., J. Photopolym Sci. Technol., 1994, 7, 619-630.
Wang et al., "Novel Anionic Photoacid Generators (PAGs) and Corresponding PAG Bound Polymers", Macromolecular Rapid Communications, 2006, 27, 18 (date Sep. 22, 2006).
Handbook of Polymer Testing: physical methods, edited by Roger Brown, 1999, 272-274.
He et al., "Micro/nanomachining of Polymer Surface for Promoting Osteoblast Cell Adhesion", Biomedical Microdevices, 5:2, 101-108, Jun. 2003.
Jin et al., "Synthesis of Biodegradeable Copolymers with Hydrophilic Functional Groups", Polymeric Materials Science and Engineering, 1997, 76, 15-16.
Pignataro et al., "Improved cell adhesion to ion beamirradiated polymer surfaces", Biomaterials, 1997, 18, 1461-1470.
Bacakova et al., "Adhesion and proliferation of cultured human aortic smooth muscle cells on polystyrene implanted with N+, F+ and Art-ions: correlation with polyer surface polarity and carbonization", Biomaterials, 1996, 17, 1121-1126.
English abstract of JP2003-322972.
English abstract of JP11-167199.
English abstract of JP2000-334881
Chem. abstract for JP 5-086133.
English abstract for JP 5-086133.
Chem. abstract for EP 473547.
He et al., Micro/nano machining of polymeric substrates by ion beam techniques, Microelectronic Engineering 65 (2003) 153-161, Elsevier Science B.V.

* cited by examiner

X = Linking group including O, -CH$_2$- , -CH$_2$-(CH$_2$)$_n$-CH$_2$- n = 0-10

X = Linking group including O, -CH$_2$- , -CH$_2$-(CH$_2$)$_n$-CH$_2$- n = 0-10

PHOTOACID GENERATORS AND LITHOGRAPHIC RESISTS COMPRISING THE SAME

RELATED APPLICATION DATA

The present application claims priority pursuant to 35 U.S.C. §119(e) to U.S. Provisional Patent Application Ser. No. 61/060,166, filed Jun. 10, 2008, and U.S. Provisional Patent Application Ser. No. 61/112,546, filed Nov. 7, 2008, both of which are incorporated herein by reference in their entireties.

FIELD OF THE INVENTION

The present invention relates to photoacid generating compounds, lithographic resists comprising photoacid generating compounds, and to various lithographic processes and applications.

BACKGROUND OF THE INVENTION

The microelectronic industry has made remarkable progress with the development of integrated circuit (IC) technology, fueled by Moore's law (Intel), which is the doubling of the number of transistors on a single chip every 2-3 years. This enables faster and more sophisticated semiconductor circuits. The exponential growth of this technology depends on the fabrication of smaller feature sizes down to the nanometer scale, forecasted as the 22 nm half pitch node.

Although EUV lithography at 13.5 nm wavelength has emerged as a promising candidate to meet the resolution requirements of the microelectronic industry roadmap, the development of advanced photoresist materials with all of the required imaging properties remains challenging and is one of the major subjects of current nanolithography research. The requirements for such photoresists include high photospeed, high resolution, low line edge roughness, low outgassing, low pattern cross-sectional aspect ratio and profile, high pattern transfer and etch resistance, low defect density, and high reproducibility. Among the foregoing, high photospeed, high resolution and low line edge/line width roughness (LER/LWR) are the most critical requirements. The design of novel resist materials that can achieve all three characteristics is the key for the progression of Moore's law via the continued success of high resolution nanopatterning in integrated circuit manufacturing.

Two primary types of resist polymers that have been investigated are chain-scission resists and pendant chemically amplified (CA) resists. Upon irradiation of a chain-scission resist film, the molecular weights of the polymers in the exposed regions are decreased via chain scission reactions arising from the irradiation. As a result, solubility differentiation is achieved between the exposed and the unexposed regions. Chemically amplified resists, however, achieve solubility differentiation based on an acid-catalyzed deprotection reaction which changes the polarity of the polymer in the exposed region. A typical CA resist formula consists of a matrix polymer and a photoacid generator (PAG). Upon irradiation with an electron beam or extreme UV radiation, the PAG generates a strong acid that catalyzes the deprotection reaction.

Several classes of PAGs have been used in CA resists. These PAGs, however, are almost exclusively used in their small molecule forms, and small molecule PAGs typically exhibit limited compatibility with the resist polymer matrix. As a result, problems such as phase separation, non-uniform acid distribution, and non-uniform acid migration occurring during temperature fluctuations (e.g. variation in baking processing) may arise. Such limitations frequently lead to an undesirable, premature and non-uniform deprotection reaction in the CA resist film.

SUMMARY

The present invention addresses several of the current limitations in lithographic techniques by providing photoacid generators and lithographic resists comprising photoacid generators which, in some embodiments, can achieve high sensitivity, high contrast, high resolution, and/or high dry etch resistance for pattern transfer to a substrate. Moreover, the present invention provides photoacid generators and resists that can address compatibility problems which can lead to phase separation, non-uniform acid distribution, and non-uniform acid migration occurring during temperature fluctuations.

In one embodiment, the present invention provides an anionic photoacid generator of Formula (I):

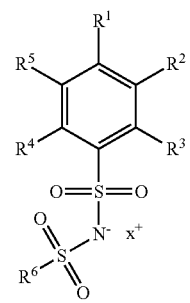

wherein $R^1$, $R^2$, $R^3$, $R^4$, $R^5$ and $R^6$ are independently selected from the group consisting of -hydrogen, -alkyl, -alkenyl, -alkynyl, -cycloalkyl, -fluoroalkyl, -fluoroalkenyl, -fluoroalkynyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, -carboxyl, -hydroxyl, -halo, -cyano and -nitro, wherein the alkyl, alkenyl, alkynyl, cycloalkyl, aryl and heteroaryl groups of $R^1$-$R^6$ are optionally and independently substituted one of more times with a substituent selected from the group consisting of -alkyl, -alkenyl, -fluoroalkyl, -fluoroalkyl, -aryl, —O-alkyl, —O-alkenyl, —O-aryl, —O-alkylene-aryl, -carboxyl, -hydroxyl, -halo, and -nitro; and $X^+$ is a compound selected from the group consisting of a sulfonium compound or an ionium compound.

In another embodiment, the present invention provides a cationic photoacid generator of Formula (II):

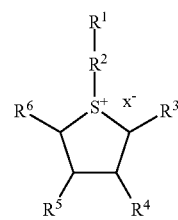

wherein

R¹ is selected from the group consisting of -hydrogen, -alkyl, -alkenyl, -alkynyl, -cycloalkyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, and —OH;

R² is selected from the group consisting of alkylene, cycloalkylene, arylene, heteroarylene and polycyclic;

R³, R⁴, R⁵ and R⁶ are independently selected from the group consisting of -hydrogen, -alkyl, -alkenyl, -alkynyl, -cycloalkyl, -aryl, -heteroaryl, —O-alkyl, —O-alkenyl, —O-aryl, —O-heteroaryl, —O-alkylene-aryl, —O-alkylene-arylene-alkyl, —O-alkylene-arylene-alkenyl;

wherein the alkyl, alkenyl, alkynl, cycloalkyl, aryl, and heteroaryl of R¹ and R³-R⁶ are optionally and independently substituted one or more times with a substituent selected from the group consisting of -alkyl, -alkenyl, -alkynyl, cycloalkyl, -aryl, heteroaryl, —O-alkyl, —O-alkenyl, —O-aryl, —O-alkylene-aryl, -carboxyl, -hydroxyl, -halo, and -nitro; and X⁻ is selected from the group consisting of $CF_3SO_3^-$, $C_4F_9SO_3^-$ and an anionic photoacid generator of Formula (I) wherein the counter cation is not present.

In another aspect, the present invention provides lithographic resists comprising photoacid generators described herein. In one embodiment, the present invention provides a lithographic resist comprising at least one photoacid generator of Formula (I). In another embodiment, the present invention provides a lithographic resist comprising at least one photoacid generator of Formula (II). In some embodiments, the present invention provides a lithographic resist comprising photoacid generators of Formulas (I) and (II).

In one embodiment, the present invention provides a lithographic resist comprising an adamantyl component and a photoacid generating component, wherein the photoacid generating component comprises at least one photoacid generator of Formula (I) and/or Formula (II). In some embodiments, the photoacid generating component comprises a plurality of photoacid generators of Formula (I) and/or Formula (II).

In some embodiments, the photoacid generating component is blended with the adamantyl component. In other embodiments, the photoacid generating component is incorporated into a polymeric chain of the lithographic resist through copolymerization with the adamantyl component.

A lithographic resist comprising an adamantyl component and a photoacid generating component, in some embodiments, further comprises a hydroxystyrene component or a γ-butyrolactone component. In some embodiments, the adamantyl component and hydroxystyrene component or γ-butyrolactone component are copolymerized.

In another embodiment, the present invention provides a lithographic resist comprising a polycarbonate and a photoacid generating component, wherein the photoacid generating component comprises at least one photoacid generator of Formula (I) and/or Formula (II). In some embodiments, the polycarbonate has a cyclic structure. Moreover, in some embodiments, the polycarbonate is operable to undergo acid-catalyzed thermolytic depolymerization. In some embodiments the photoacid generating component is blended with the polycarbonate. In other embodiments, the photoacid generating component is incorporated into the polymeric chain of the polycarbonate. In some embodiments, the photoacid generating component is incorporated into the polymeric chain of the polycarbonate by chemical reaction with one or more functional or linking groups associated with the polymeric chain.

In another aspect, the present invention provides one or a plurality of acid amplifiers for use in a chemically amplified lithographic resist. An acid amplifier works in conjunction with a photoacid generator to produce additional acid for the deprotection reaction resulting in a polarity change of the chemically amplified resist. In some embodiments, the present invention provides an acid amplifier of Formula (III):

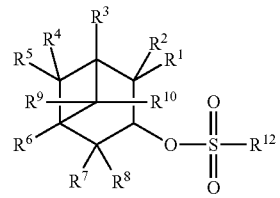

wherein

R¹, R², R³, R⁴, R⁵, R⁶, R⁷, R⁸, R⁹, R¹⁰ and R¹² are independently selected from the group consisting of -hydrogen, -alkyl, -alkenyl, -alkynyl, -cycloalkyl, -fluoroalkyl, -fluoroalkenyl, -fluoroalkynyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, -carboxyl, -hydroxyl, -halo, -cyano and -nitro, wherein the alkyl, alkenyl, alkynyl, cycloalkyl, aryl and heteroaryl groups of R¹-R⁸ are optionally and independently substituted one of more times with a substituent selected from the group consisting of -alkyl, -alkenyl, -fluoroalkyl, -fluoroalkyl, -aryl, —O-alkyl, —O-alkenyl, —O-aryl, —O-alkylene-aryl, —OC(O)-alkyl, —OC(O)-alkenyl, -carboxyl, -hydroxyl, -halo, and -nitro.

In another aspect, the present invention provides a lithographic resist comprising an acid amplifier of Formula (III). In some embodiments, one or a plurality of acid amplifiers are blended into lithographic resists. In other embodiments, one or a plurality of acid amplifiers are incorporated into a polymeric backbone of the resist through copolymerization with monomers constructing the resist. Moreover, in some embodiments, a lithographic resist comprising an acid amplifier of Formula (III) further comprises a photoacid generator of Formula (I) and/or Formula (II). As provided herein, the photoacid generator of Formula (I) and/or Formula (II) can be blended into the lithographic resist comprising the acid amplifier of Formula (III) or incorporated into a polymeric chain of the resist through copolymerization with the acid amplifier as well as other chemical species of the resist such as an adamantyl component and/or a hydroxystyrene component.

In a further aspect the present invention provides one or a plurality of energy harvesting units for use in a chemically amplified resist. Energy harvesting units, in some embodiments, enhance the acid quantum yield of the lithographic resist by capturing greater amounts of the electromagnetic radiation striking the resist during a lithographic process. In some embodiments, an energy harvesting unit is blended into a lithographic resist comprising a photoacid generating component. In other embodiments, an energy harvesting unit is incorporated into a polymeric chain of the resist by copolymerization with other chemical species of the resist such as a photoacid generator, adamantyl component, hydroxystyrene component or combinations thereof.

Energy harvesting units, in some embodiments, comprise conjugated chemical species including conjugated polymers. In some embodiments, conjugated polymers comprise polythiophenes, polyphenylene vinylene (PPV), poly(2-vinylpyridine) (P2VP), polyamides, poly(N-vinylcarbazole) (PVCZ), polypyrrole (PPy), and polyaniline (PAn). In some embodiments, conjugated chemical species comprise pyrroles, furans, thiophenes, imidazoles, thiazoles, pyridines, pyrimidines, quinolines, isoquinolines, indoles, purines, and other fused ring aromatic species.

In another aspect, the present invention provides a lithographic resist comprising at least one energy harvesting unit. In some embodiments, a lithographic resist comprising at least one energy harvesting unit further comprises a photoacid generator. In some embodiments, a photoacid generator comprises a photoacid generator of Formula (I) or Formula (II). In some embodiments, as provided herein, the photoacid generator is blended into the lithographic resist or incorporated into a polymeric chain of the resist. Alternatively, in some embodiments, a photoacid generator is pendantly bound to an energy harvesting unit wherein the photoacid generator is not in the backbone of a polymeric chain of the resist.

In some embodiments, a lithographic resist comprising at least one energy harvesting unit and photoacid generator further comprises an acid amplifier as described herein. In some embodiments, an acid amplifier is blended into the resist or incorporated into a polymeric chain of the resist.

In a further aspect, the present invention provides a lithographic resist comprising at least one adhesion unit. An adhesion unit, in some embodiments, enhances the adhesion of a lithographic resist to a substrate.

In some embodiments, a lithographic resist of the present invention has an acid generation efficiency greater than about 70%. In another embodiment, a lithographic resist has an acid generation efficiency greater than about 75% or greater than about 80%. In some embodiments, a lithographic resist has an acid generation efficiency greater than about 85% or greater than about 90%. Acid generation efficiencies of lithographic resists of the present invention can be determined according to procedures described herein.

In another aspect, the present invention provides lithographic processes. In one embodiment, a lithographic process of the present invention comprises exposing a lithographic recording medium to radiation to form a pattern, wherein the lithographic recording medium comprises a resist as described herein. In some embodiments, a lithographic process further comprises developing the pattern. In some embodiments of lithographic processes of the present invention, radiation used in the patterning of resists comprises extreme ultraviolet radiation (EUV), x-ray radiation, 193 nm radiation, electron beam radiation, ion beam radiation, or combinations thereof.

In another aspect, the present invention provides integrated circuits prepared by lithographic processes utilizing the presently described resists.

These and other features, embodiments, objects and advantages of the present invention will become apparent after a review of the following detailed description of the disclosed embodiments.

DETAILED DESCRIPTION

The present invention can be understood more readily by reference to the following detailed description, examples and drawings and their previous and following descriptions. Compositions and methods of the present invention, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In one embodiment, the present invention provides an anionic photoacid generator of Formula (I):

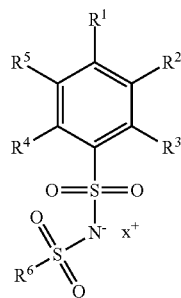

wherein $R^1$, $R^2$, $R^3$, $R^4$, $R^5$ and $R^6$ are independently selected from the group consisting of -hydrogen, -alkyl, -alkenyl, -alkynyl, -cycloalkyl, -fluoroalkyl, -fluoroalkenyl, -fluoroalkynyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, -carboxyl, -hydroxyl, -halo, -cyano and -nitro, wherein the alkyl, alkenyl, alkynyl, cycloalkyl, aryl and heteroaryl groups of $R^1$-$R^6$ are optionally and independently substituted one or more times with a substituent selected from the group consisting of -alkyl, -alkenyl, -fluoroalkyl, -fluoroalkyl, -aryl, —O-alkyl, —O-alkenyl, —O-aryl, —O-alkylene-aryl, -carboxyl, -hydroxyl, -halo, and -nitro; and $X^+$ is a compound selected from the group consisting of a sulfonium compound or an ionium compound.

Sulfonium compounds, according to some embodiments of the present invention, have the formula:

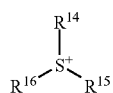

wherein $R^{14}$, $R^{15}$, and $R^{16}$ are independently selected from the group consisting of -alkyl and -aryl, wherein the aryl is optionally substituted 1 to 5 times with a substituent group, wherein the substituent group(s) are independently selected from the group consisting of -alkyl and -aryl.

Ionium compounds, according to some embodiments of the present invention, have the formula:

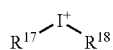

wherein $R^{17}$ and $R^{18}$ are independently selected from the group consisting of -alkyl and -aryl, wherein the aryl is optionally substituted 1 to 5 times with a substituent group, wherein the substituent group(s) are independently selected from the group consisting of -alkyl and -aryl.

Figure 1:
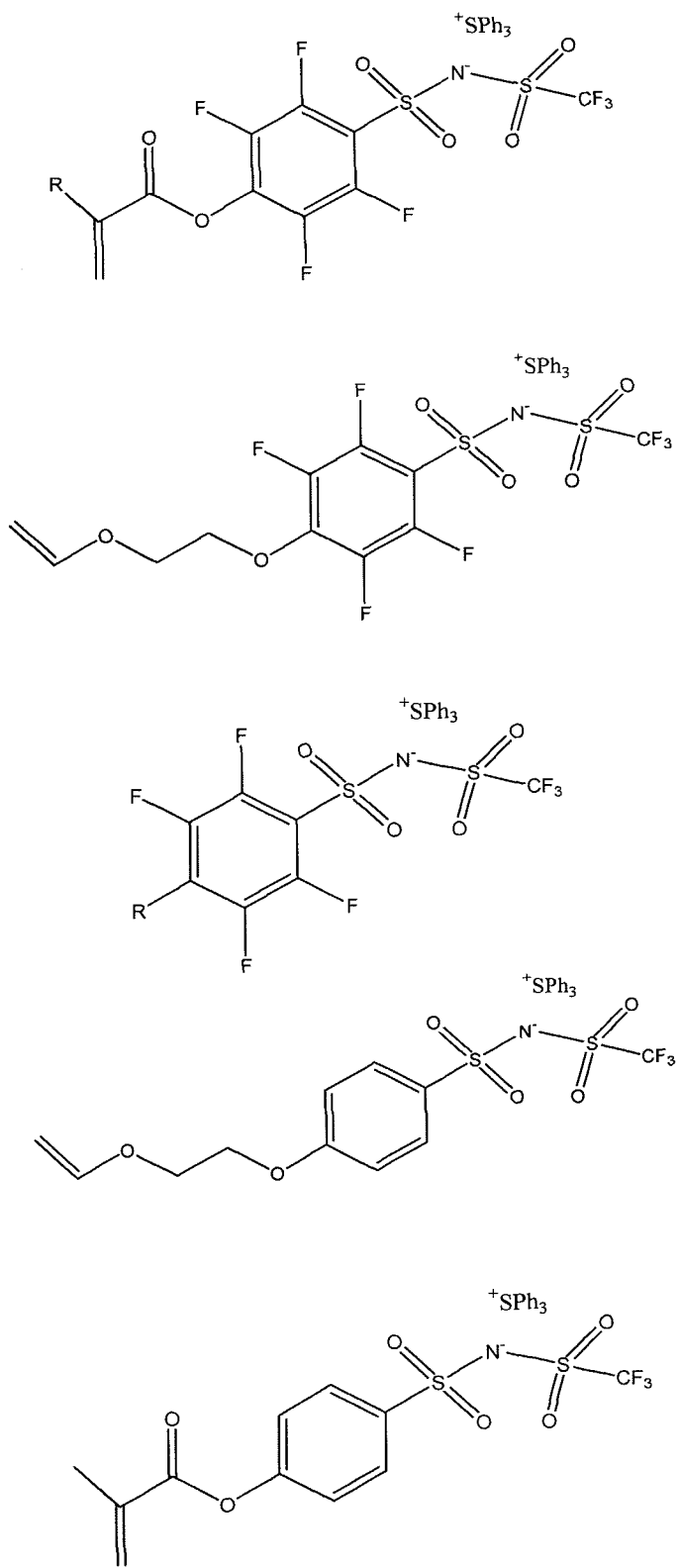
FIG. 1 illustrates various photoacid generators of Formula (I) according some embodiments of the present invention.
Figure 2:
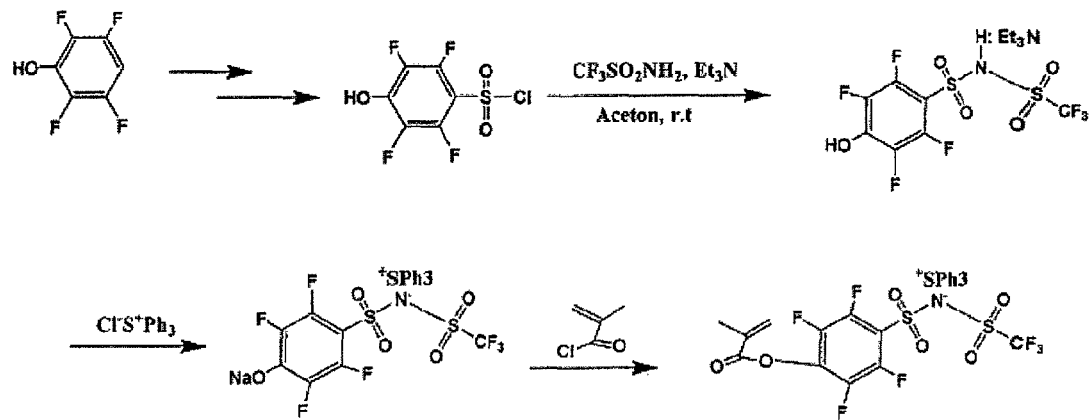
FIG. 2 illustrates a synthetic scheme for producing a photoacid generator of Formula (I) according to one embodiment of the present invention.
Figure 20:
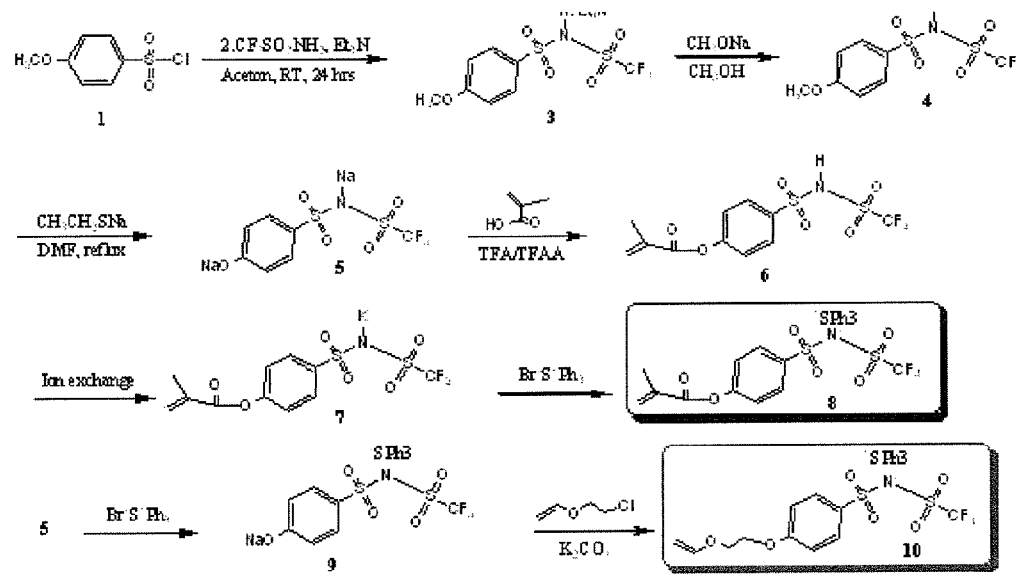
FIG. 20 illustrates a synthetic scheme for producing a photoacid generator of Formula (I) according to one embodiment of the present invention.

Non-limiting examples of photoacid generators of Formula (I) are provided in FIG. 1. R in the non-limiting examples provided in the FIG. 1, in some embodiments, is selected from the group consisting of hydrogen, —OC(O)-alkyl, —NO$_2$ and -halo. Moreover, FIGS. 2 and 20 illustrate various non-limiting synthetic schemes for producing a photoacid generator of Formula (I) according to one embodiment of the present invention.

In another embodiment, the present invention provides a cationic photoacid generator of Formula (II):

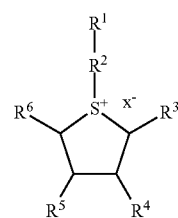

wherein $R^1$ is selected from the group consisting of -hydrogen, -alkyl, -alkenyl, -alkynyl, -cycloalkyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, and —OH;

$R^2$ is selected from the group consisting of alkylene, cycloalkylene, arylene, heteroarylene and polycyclic;

$R^3$, $R^4$, $R^5$ and $R^6$ are independently selected from the group consisting of -hydrogen, -alkyl, -alkenyl, -alkynyl, -cycloalkyl, -aryl, -heteroaryl, —O-alkyl, —O-alkenyl, —O-aryl, —O-heteroaryl, —O-alkylene-aryl, —O-alkylene-arylene-alkyl, —O-alkylene-arylene-alkenyl;

wherein the alkyl, alkenyl, alkynl, cycloalkyl, aryl, and heteroaryl of $R^1$ and $R^3$-$R^6$ are optionally and independently substituted one or more times with a substituent selected from the group consisting of -alkyl, -alkenyl, -alkynyl, cycloalkyl, -aryl, heteroaryl, —O-alkyl, —O-alkenyl, —O-aryl, —O-alkylene-aryl, -carboxyl, -hydroxyl, -halo, and -nitro; and $X^-$ is selected from the group consisting of $CF_3SO_3^-$, $C_4F_9SO_3^-$ and an anionic photoacid generator of Formula (I) wherein the counter cation is not present.

Figure 3:
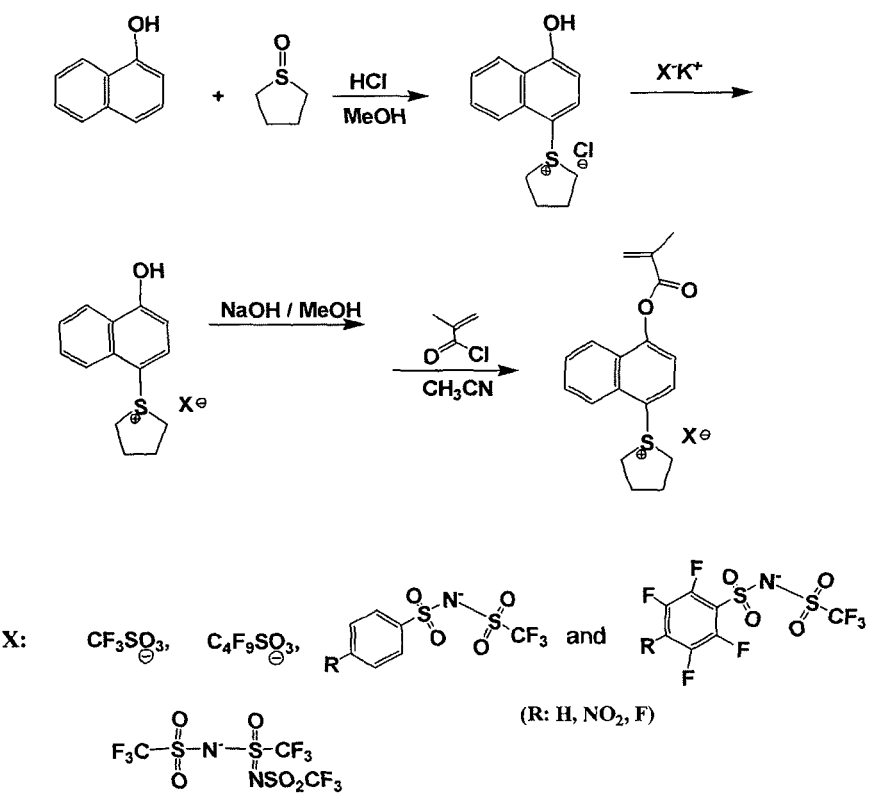
FIG. 3 illustrates a synthetic scheme for producing a photoacid generator of Formula (II) according to one embodiment of the present invention.

FIG. 3 illustrates a synthetic scheme for producing a photoacid generator of Formula (II) according to one embodiment of the present invention.

In another aspect, the present invention provides lithographic resists comprising photoacid generators described herein. In one embodiment, the present invention provides a lithographic resist comprising at least one photoacid generator of Formula (I). In another embodiment, the present invention provides lithographic resist comprising at least one photoacid generator of Formula (II). In some embodiments, the present invention provides a lithographic resist comprising a photoacid generator component of Formula (I) and Formula (II)

In one embodiment, the present invention provides a lithographic resist comprising an adamantyl component and a photoacid generating component, wherein the photoacid generating component comprises at least one photoacid generator of Formula (I) and/or Formula (II). In some embodiments, the photoacid generating component comprises a plurality of photoacid generators of Formula (I) and/or Formula (II).

In some embodiments, the photoacid generating component is blended with the adamantyl component. In other embodiments, the photoacid generating component is incorporated into a polymeric chain of the polymeric resist through copolymerization with the adamantyl component.

A lithographic resist comprising an adamantyl component and a photoacid generating component, in some embodiments, further comprises a hydroxystyrene component or a γ-butyrolactone component. In some embodiments, the adamantyl component and hydroxystyrene component or γ-butyrolactone component are copolymerized.

In another embodiment, the present invention provides a lithographic resist comprising a polycarbonate and a photoacid generating component, wherein the photoacid generating component comprises at least one photoacid generator of Formula (I) and/or Formula (II). In some embodiments, the polycarbonate has a cyclic structure. Moreover, in some embodiments, the polycarbonate is operable to undergo acid-catalyzed thermolytic depolymerization. In some embodiments the photoacid generating component is blended with the polycarbonate. In other embodiments, the photoacid generating component is incorporated into the polymeric chain of the polycarbonate. In some embodiments, the photoacid generating component is incorporated into the polymeric chain of the polycarbonate by chemical reaction with one or more functional or linking groups associated with the polymeric chain.

Figure 17:
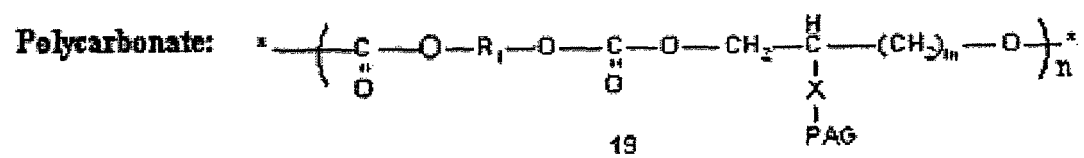
FIG. 17 illustrates a lithographic resist comprising a polycarbonate having a photoacid generator incorporated into the polymeric chain according to one embodiment of the present invention.

FIG. 17 illustrates a lithographic resist comprising a polycarbonate having a photoacid generator incorporated into the polymeric chain according to one embodiment of the present invention. In the embodiment illustrated in FIG. 17, the photoacid generator is incorporated into the polymeric chain of the polycarbonate through a linking group.

Figure 18:
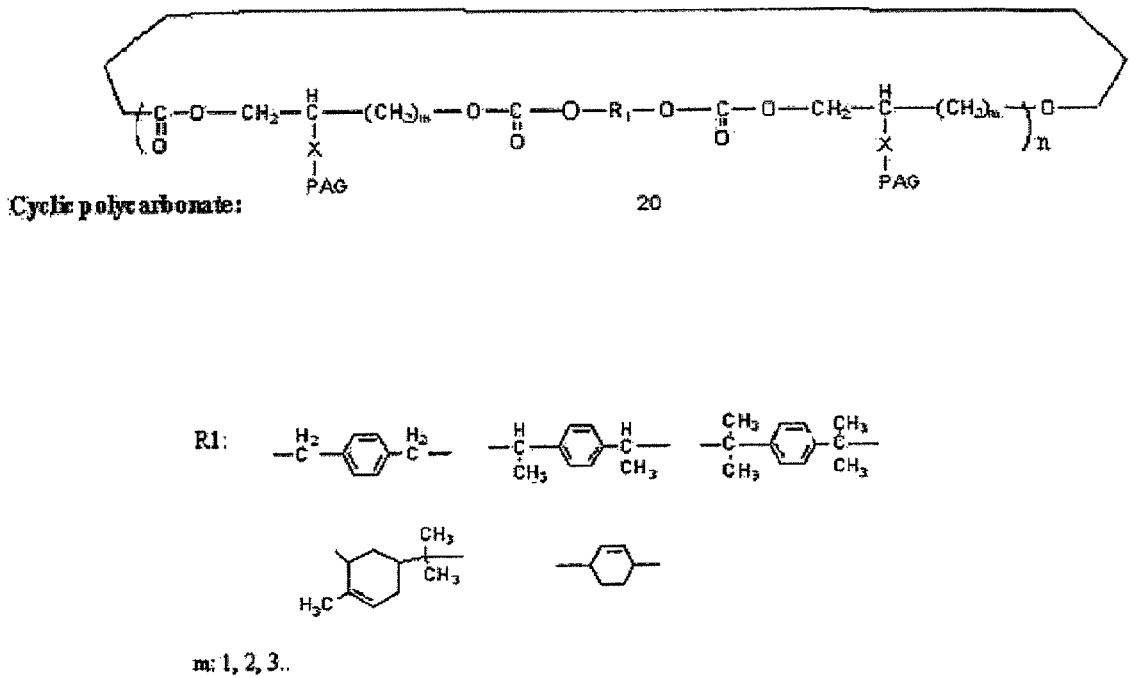
FIG. 18 illustrates a lithographic resist comprising a cyclic polycarbonate having a photoacid generator incorporated into the polymeric chain according to one embodiment of the present invention.

FIG. 18 illustrates a lithographic resist comprising a cyclic polycarbonate having a photoacid generator incorporated into the polymeric chain according to one embodiment of the present invention. In the embodiment illustrated in FIG. 18, the photoacid generator is incorporated into the polymeric chain of the polycarbonate through a linking group.

Figure 19:
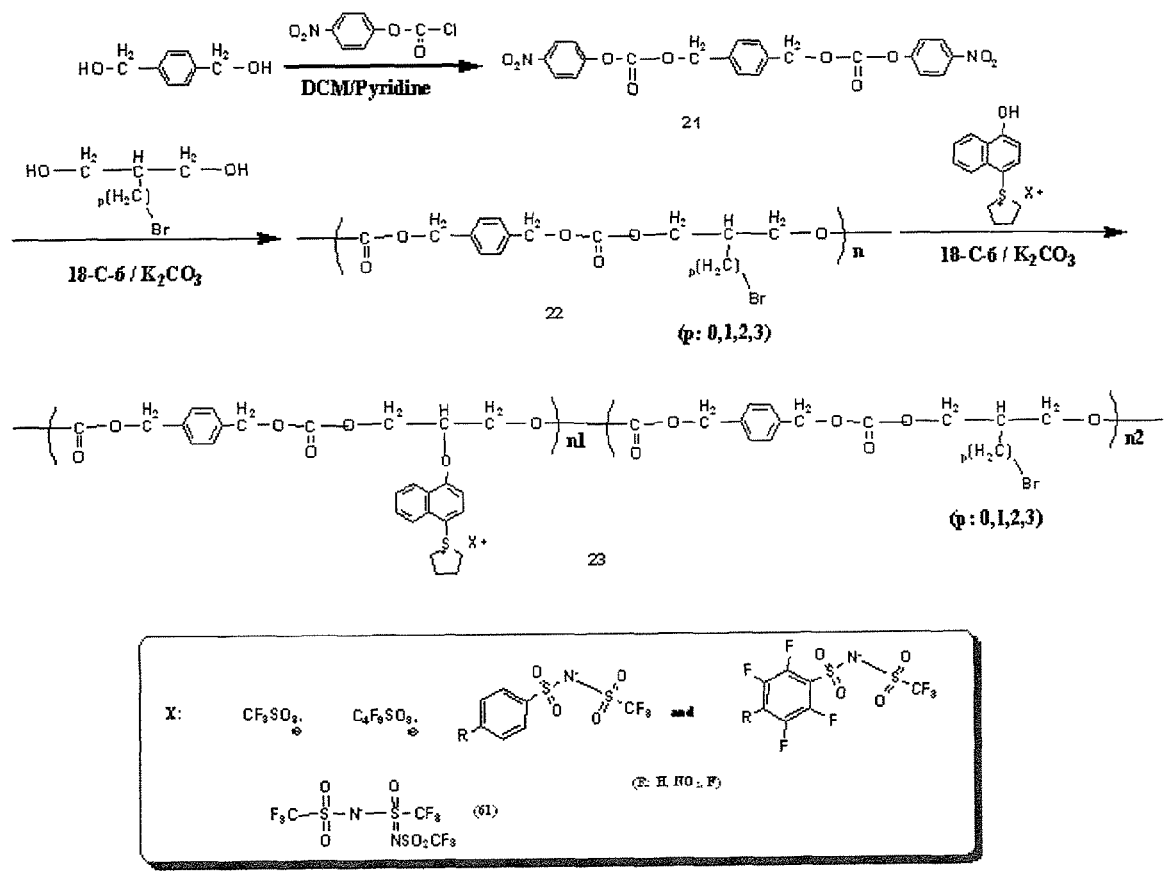
FIG. 19 illustrates a synthetic scheme for producing a lithographic resist comprising a polycarbonate having a photoacid generator incorporated into the polymeric chain of the polycarbonate according to one embodiment of the present invention.

FIG. 19 illustrates a synthetic scheme for producing a lithographic resist comprising a polycarbonate having a photoacid generator incorporated into the polymeric chain of the polycarbonate according to one embodiment of the present invention. In FIG. 19, a photoacid generator of Formula (II) is reacted with a bromine functionality pendant to the backbone of the polycarbonate to bind the photoacid generator to the polycarbonate chain. Numerous polycarbonates possessing the desired structural features can be prepared from a variety of diols, the polycarbonates suitable for blending or reacting with a photoacid generator of the present invention.

Figure 4:
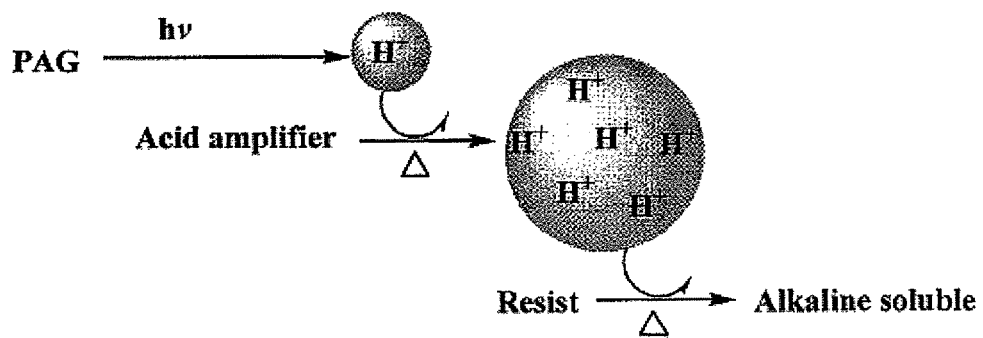
FIG. 4 illustrates a mechanistic pathway for the operation of an acid amplifier according to one embodiment of the present invention.

In another aspect, the present invention provides one or a plurality of acid amplifiers for use in a chemically amplified lithographic resist. As illustrated in FIG. 4, an acid amplifier works in conjunction with a photoacid generator to produce additional acid for the deprotection reaction resulting in a polarity change of the chemically amplified resist. In some embodiments, the present invention provides an acid amplifier of Formula (III):

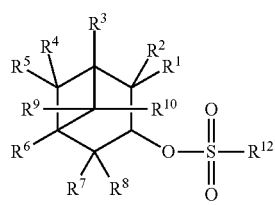

wherein
$R^1$, $R^2$, $R^3$, $R^4$, $R^5$, $R^6$, $R^7$, $R^8$, $R^9$, $R^{10}$ and $R^{12}$ are independently selected from the group consisting of
-hydrogen, -alkyl, -alkenyl, -alkynyl, -cycloalkyl, -fluoroalkyl, -fluoroalkenyl, -fluoroalkynyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, -carboxyl, -hydroxyl, -halo, -cyano and -nitro,
wherein the alkyl, alkenyl, alkynyl, cycloalkyl, aryl and heteroaryl groups of $R^1$-$R^8$ are optionally and independently substituted one of more times with a substituent selected from the group consisting of -alkyl, -alkenyl, -fluoroalkyl, -fluoroalkyl, -aryl, —O-alkyl, —O-alkenyl, —O-aryl, —O-alkylene-aryl, —OC(O)-alkyl, —OC(O)-alkenyl, -carboxyl, -hydroxyl, -halo, and -nitro.

Figure 5:
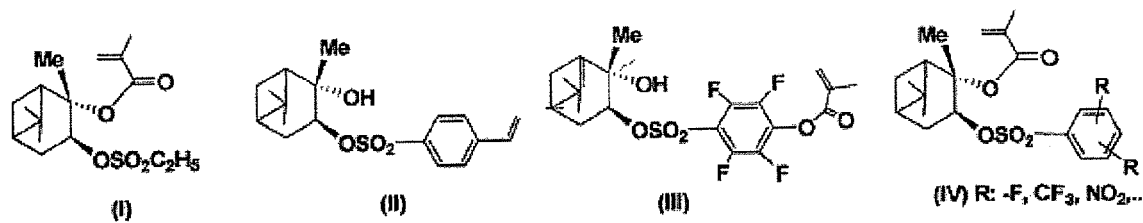
FIG. 5 illustrates various acid amplifiers of Formula (III) according to some embodiments of the present invention.
Figure 6:
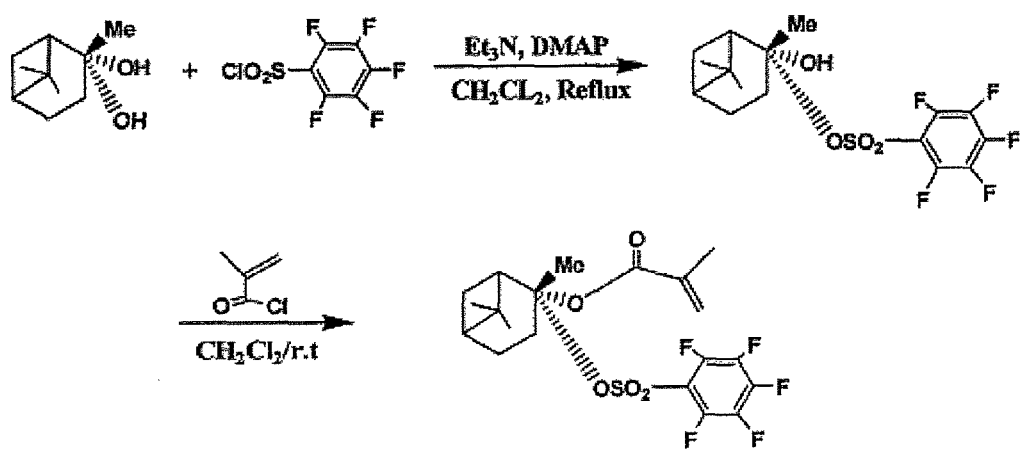
FIG. 6 illustrates a synthetic scheme for producing an acid amplifier of Formula (III) according to one embodiment of the present invention.

FIG. 5 illustrates various acid amplifiers of Formula (III) according to some embodiments of the present invention. Moreover, FIG. 6 illustrates a synthetic scheme for producing a acid amplifier according to one embodiment of the present invention.

In another aspect, the present invention provides a lithographic resist comprising an acid amplifier of Formula (III). In some embodiments, one or a plurality of acid amplifiers are blended into lithographic resists. In other embodiments, one or a plurality of acid amplifiers are incorporated into a polymeric backbone of the resist through copolymerization with monomers constructing the resist. Acid amplifiers, in some embodiments, can be copolymerized with other monomers constructing the resist by radical polymerization techniques.

Moreover, in some embodiments, a lithographic resist comprising an acid amplifier of Formula (III) further comprises a photoacid generator of Formula (I) and/or Formula (II). As provided herein, a photoacid generator of Formula (I) and/or Formula (II) can be blended into the lithographic resist comprising the acid amplifier of Formula (III) or incorporated into a polymeric chain of the resist through copolymerization with the acid amplifier as well as other chemical species of the resist such as an adamantyl component and/or a hydroxystyrene component. In some embodiments, an acid amplifier of Formula (III), a photoacid generator of Formula (I) and/or Formula (II) as well as other chemical species of the resist such as an adamantyl component and/or a hydroxystyrene component can be copolymerized by radical polymerization techniques.

Figure 7:
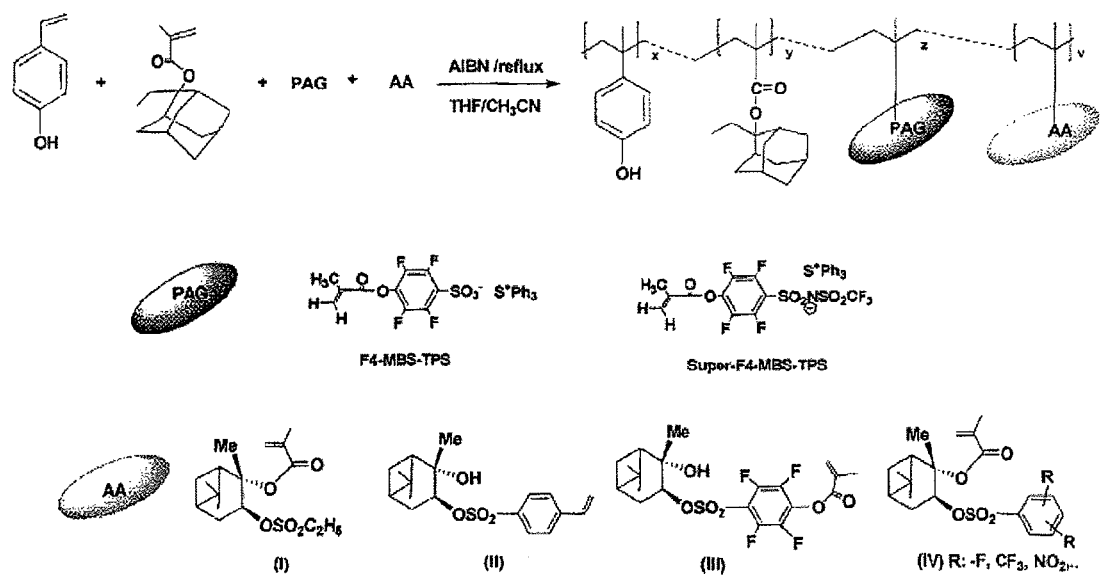
FIG. 7 illustrate a lithographic resist comprising a hydroxystyrene component, adamantyl component, photoacid generator and acid amplifier according to one embodiment of the present invention.

FIG. 7 illustrates a lithographic comprising a hydroxystyrene component, adamantyl component, photoacid generator and acid amplifier according to one embodiment of the present invention. As displayed in FIG. 7, the hydroxystyrene component, adamantyl component, photoacid generator and acid amplifier are copolymerized in the production of the lithographic resist.

In a further aspect the present invention provides one or a plurality of energy harvesting units for use in a chemically amplified resist. Energy harvesting units, in some embodiments, enhance the acid quantum yield of the lithographic resist by capturing greater amounts of the electromagnetic radiation striking the resist during a lithographic process. In some embodiments, an energy harvesting unit is blended into a lithographic resist comprising a photoacid generating component. In other embodiments, an energy harvesting unit is incorporated into a polymeric chain of the resist by copolymerization with other chemical species of the resist such as a photoacid generator, adamantyl component, hydroxystyrene component or combinations thereof. In some embodiments, energy harvesting units can be copolymerized with other components of a lithographic resist by radical polymerization techniques.

Energy harvesting units, in some embodiments, comprise conjugated chemical species including conjugated polymers. In some embodiments, conjugated polymers comprise polythiophenes, polyphenylene vinylene (PPV), poly(2-vinylpyridine) (P2VP), polyamides, poly(N-vinylcarbazole) (PVCZ), polypyrrole (PPy), and polyaniline (PAn). In some embodiments, conjugated chemical species comprise pyrroles, furans, thiophenes, imidazoles, thiazoles, pyridines, pyrimidines, quinolines, isoquinolines, indoles, purines, and other fused ring aromatic species.

Figure 8:
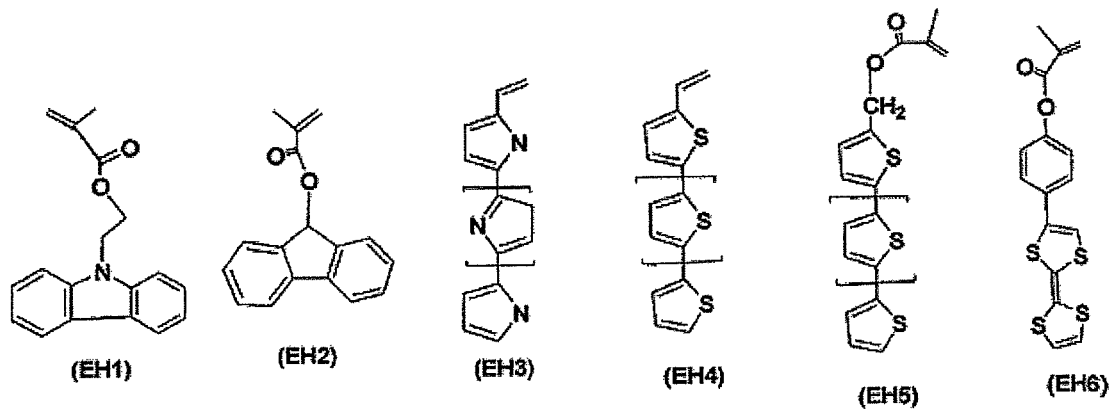
FIG. 8 illustrates various energy harvesting units according to some embodiments of the present invention.

FIG. 8 illustrates various energy harvesting units according to some embodiments of the present invention.

Figure 9:
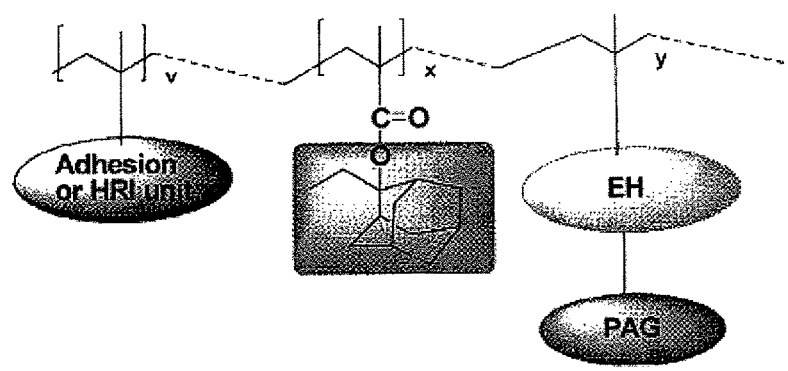
FIG. 9 illustrates a lithographic resist comprising an adhesion unit, adamantyl component and energy harvesting unit having a photoacid generator bound thereto according to one embodiment of the present invention.

In another aspect, the present invention provides a lithographic resist comprising at least one energy harvesting unit. In some embodiments, a lithographic resist comprising at least one energy harvesting unit further comprises a photoacid generator. In some embodiments, a photoacid generator comprises a photoacid generator of Formula (I) or Formula (II). In some embodiments, as provided herein, the photoacid generator is blended into the lithographic resist or incorporated into a polymeric chain of the resist. Alternatively, in some embodiments, a photoacid generator is pendantly bound to an energy harvesting unit wherein the photoacid generator is not in the backbone of a polymeric chain of the resist as illustrated in FIG. 9.

Figure 10:
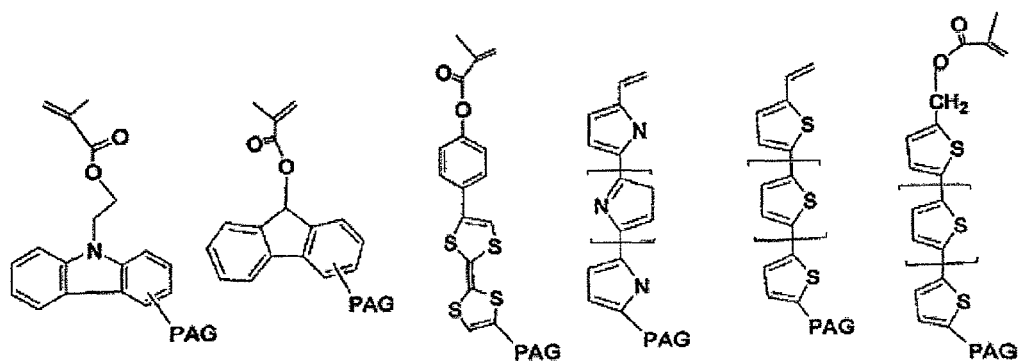
FIG. 10 illustrates various energy harvesting units having a photoacid generator bound thereto according to some embodiments of the present invention.

FIG. 10 illustrates various energy harvesting units having a photoacid generator bound thereto according to some embodiments of the present invention. In some embodiments, the photoacid generator (PAG) bound to an energy harvesting unit of FIG. 10 has the formula:

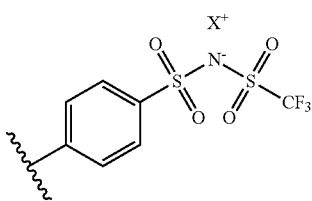

wherein

is a point of attachment of the PAG to the energy harvesting unit and $X^+$ is defined herein. In another embodiment, the PAG bound to the energy harvesting unit of FIG. 10 has the formula:

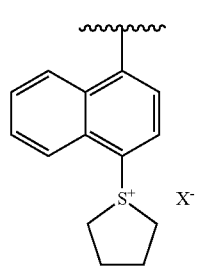

wherein

is a point of attachment of the PAG to the energy harvesting unit and $X^-$ is defined herein.

Figure 11:
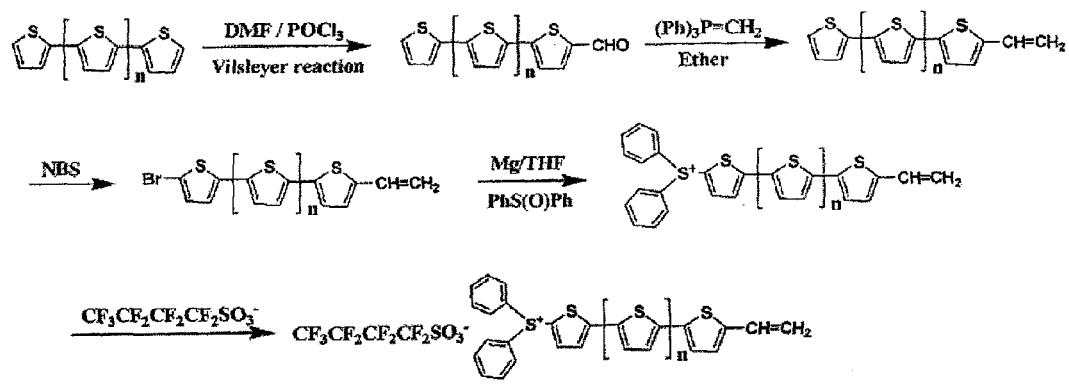
FIG. 11 illustrates a synthetic scheme for producing an energy harvesting unit having a photoacid generator bound thereto according to one embodiment of the present invention.
Figure 12:
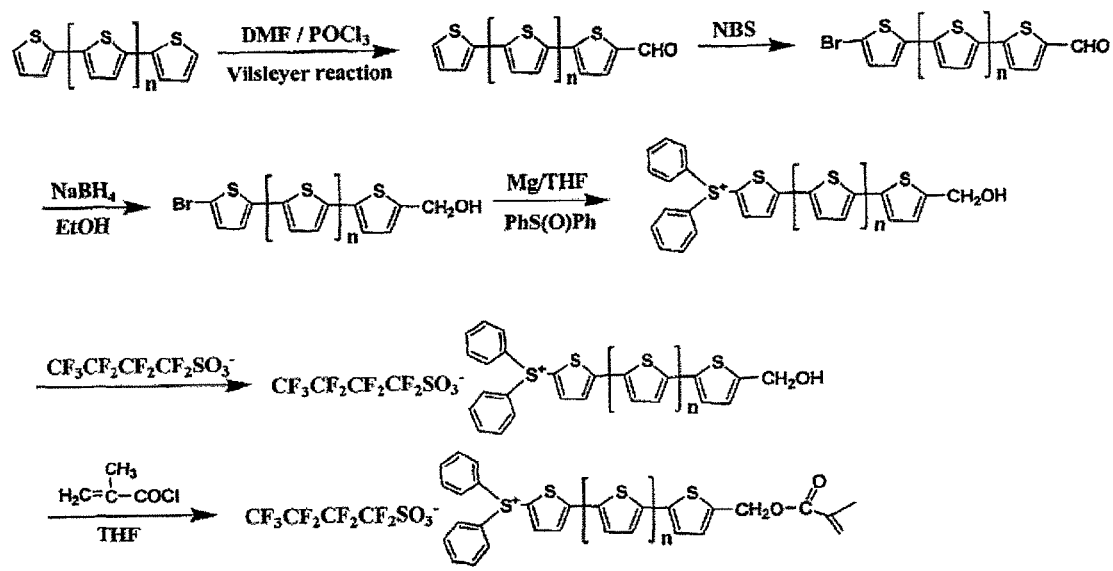
FIG. 12 illustrates a synthetic scheme for producing an energy harvesting unit having a photoacid generator bound thereto according to one embodiment of the present invention.

Moreover, FIGS. 11 and 12 provide synthetic schemes for producing energy harvesting units having a photoacid generator bound thereto.

Figure 13:
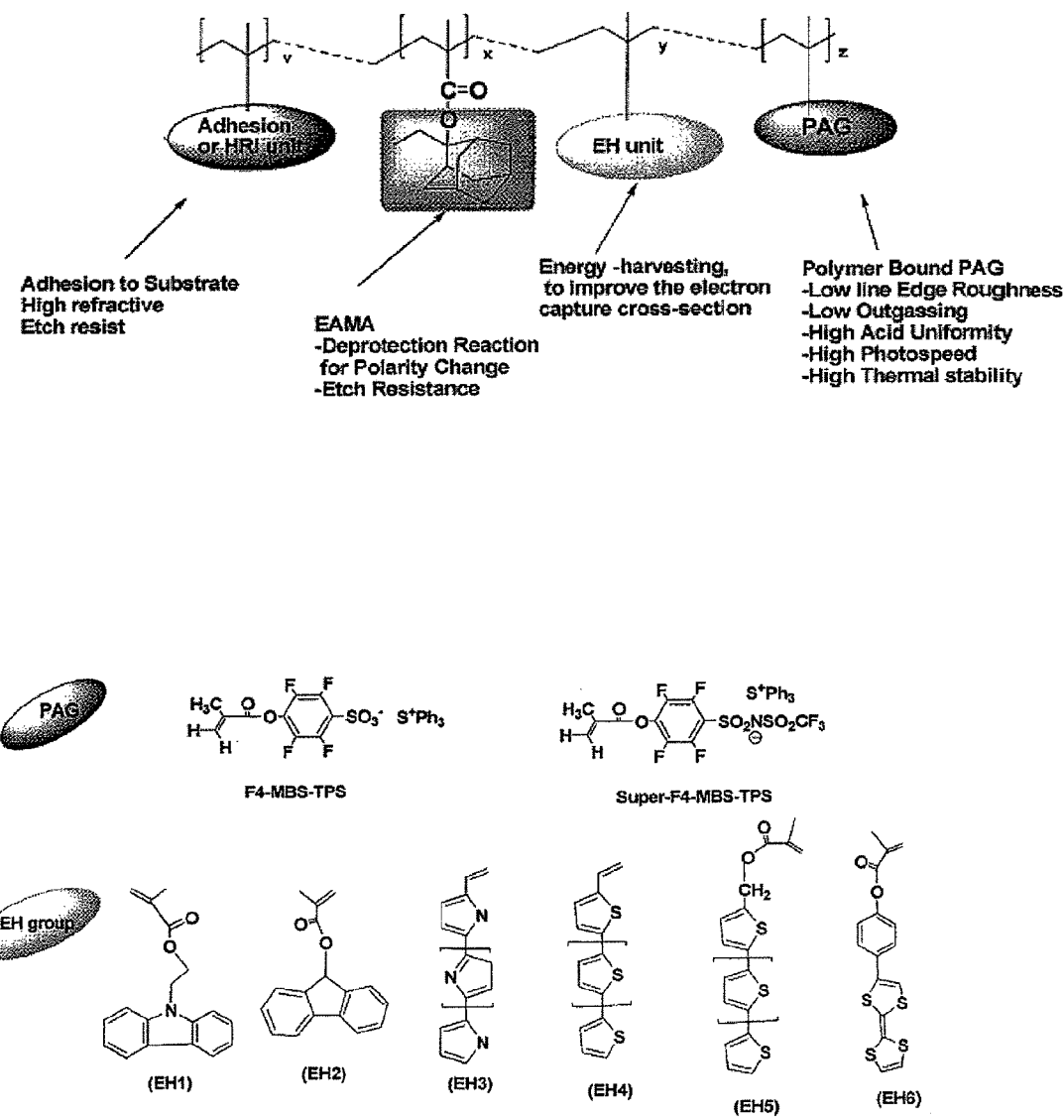
FIG. 13 illustrates a lithographic resist comprising an adhesion unit, adamantyl component, energy harvesting unit and photoacid generator according to one embodiment of the present invention.

In some embodiments, a lithographic resist comprising at least one energy harvesting unit further comprises an acid amplifier as described herein. In some embodiments, an acid amplifier is blended into the resist and/or incorporated into a polymeric chain of the resist. FIG. 13 illustrates a lithographic resist comprising an adhesion unit, adamantyl component, energy harvesting unit and photoacid generator according to one embodiment of the present invention.

In a further aspect, the present invention provides a lithographic resist comprising at least one adhesion unit. An adhesion unit, in some embodiments, enhances the adhesion of a lithographic resist to a substrate.

In another aspect, the present invention provides lithographic processes. In one embodiment, a lithographic process of the present invention comprises exposing a lithographic recording medium to radiation to form a pattern, wherein the lithographic recording medium comprises any resist described herein. In some embodiments, a lithographic process further comprises developing the pattern. In some embodiments of lithographic processes of the present invention, radiation used in the patterning of resists comprises extreme ultraviolet radiation (EUV), x-ray radiation, 193 nm radiation, electron beam radiation, ion beam radiation, or combinations thereof.

In another aspect, the present invention provides integrated circuits prepared by lithographic processes utilizing the presently described resists.

Some exemplary embodiments of the present invention will now be illustrated in the following specific, non-limiting examples.

EXAMPLE 1

Synthesis of a Photoacid Generator of Formula (I)

4-Nitrobenzenesulfonyl chloride (1, 0.01 mol) was slowly added dropwise via addition funnel to a solution of triethylamine (0.03 mol) and trifluoromethanesulfonamide (2, 0.011 mol) in 25 mL freshly distillated acetone, and the solution stirred at room temperature for 48 hours. The resulting mixture was concentrated via reduced pressure rotary evaporation. To the residue was added 25 mL 1.0 M HCl and the solution extracted with methylene chloride three times. The organic extracts were combined, dried over anhydrous sodium sulfate, and solvent were removed via reduced pressure rotary evaporation followed by further drying for 72 hours at vacuum to give product yielding 92% of brown wax which was characterized as the triethylammonium salt (3).

Figure 14:
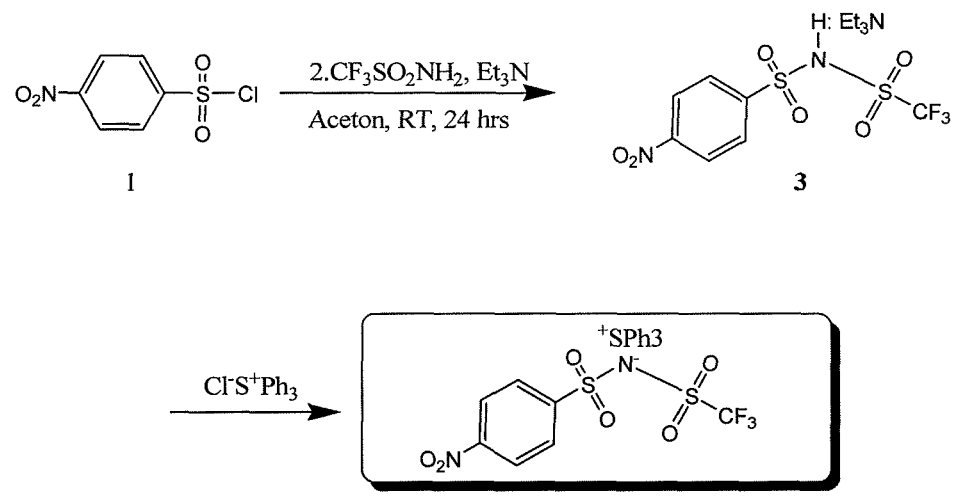
FIG. 14 illustrates a synthetic scheme for producing a photoacid generator of Formula (I) according to one embodiment of the present invention.

This salt was next reacted with 50% aqueous solution of triphenylsulfonium chloride (0.012 mol) in acetonitrile, at room temperature overnight. The resulting mixture was concentrated via reduced pressure rotary evaporation to remove acetonitrile. To the residue was extracted with methylene chloride three times. The organic extracts were combined, dried over anhydrous sodium sulfate, and solvent were removed via reduced pressure rotary evaporation followed by further drying for 72 hours at vacuum to give product yielding 87% of colorless crystal which was characterized as the final product. FIG. 14 illustrates the foregoing synthesis. $^1$H NMR (25° C., DMSO-$d_6$, ppm) δ8.32 (d, J=9.5 Hz, 2H), 8.01 (d, J=9.5 Hz, 2H), 7.38-7.86 (m, 15H). $^{13}$C NMR (25° C., DMSO-$d_6$, ppm) δ 150.5, 147.8, 141.0, 134.5, 132.4, 132.2, 131.5, 131.1, 130.5, 130.1, 128.1, 127.5, 125.6, 124.0. $^{19}$F NMR (25° C., DMSO-$d_6$, ppm, ext. CF$_3$COOH): δ −77.5 to −78.5. Anal. Calcd for $C_{25}H_{19}F_3N_2O_6S_3$: C, 50.06; H, 3.06; N, 4.43. Found: C, 50.31; H, 3.21; N, 4.70.

EXAMPLE 2

Synthesis of a Photoacid Generator of Formula (I)

4-Methoxybenzenesulfonyl chloride (1, 0.01 mol) was slowly added dropwise via addition funnel to a solution of triethylamine (0.03 mol) and trifluomethanesulfonamide (2, 0.011 mol) in 25 mL freshly distilled acetone, and the solution stirred at room temperature for 48 hours. The resulting mixture was concentrated via reduced pressure rotary evaporation. To the residue was added 25 mL 1.0 M HCl and the solution extracted with methylene chloride three times. The organic extracts were combined, dried over anhydrous sodium sulfate, and solvent were removed via reduced pressure rotary evaporation followed by further drying for 72 hours at vacuum to give product yielding 92% of brown oil which was characterized as the triethylammonium salt (3). This salt was next dissolved in 80 mL DMF and sodium ethanethiolate (0.025 mol) added. The reaction was keep reflux for 4 hours, and then the bulk DMF was removed via vacuum distillation. The remaining residue was then dissolved in 25 mL DI water and 25 mL brine added. The aqueous solution was then extracted with 50 mL portion THF that were discarded. The aqueous solution was then reacted with 50% aqueous solution of triphenylsulfonium chloride (0.012 mol) at room temperature overnight. The resulting mixture was extracted with methylene chloride three times. The organic extracts were combined, dried over anhydrous sodium sulfate, and solvent were removed via reduced pressure rotary evaporation followed by further drying for 72 hours at vacuum to give product yielding 78% of colorless crystal which was characterized as the intermediate (5). $^1$H NMR (25° C., DMSO-$d_6$, ppm) δ6.50 (d, J=7.6 Hz, 2H), 7.38 (d, J=7.6 Hz, 2H), 7.50-7.85 (m, 15H).

Figure 15:
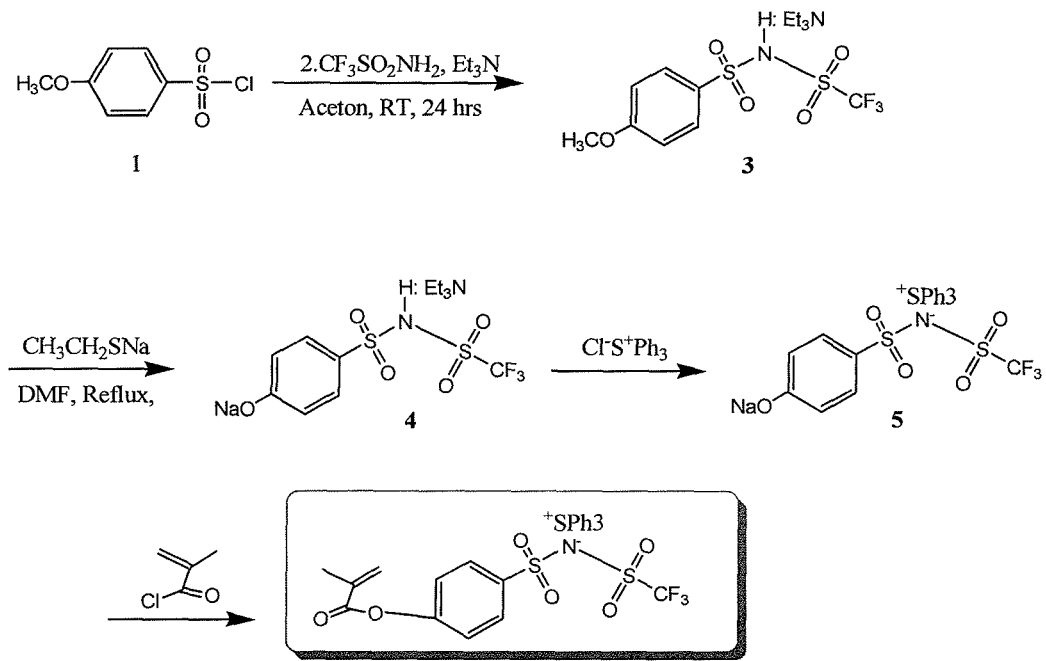
FIG. 15 illustrates a synthetic scheme for producing a photoacid generator of Formula (I) according to one embodiment of the present invention.

The intermediate (5) (5.0 mmol) was dissolved in 10 ml dried dichloromethane. Methacryloyl chloride (6.0 mmol in 3 ml dichloromethane) was added dropwise at 0° C. under nitrogen flow, then warmed to room temperature, kept it for 2 days. Then the solution was washed with DI water, and the organic layer was dried over sodium sulfate. On removal of the solvent, the product was obtained and dried under vacuum to get pale-yellow oil in yield of 75%. FIG. 15 illustrates the foregoing synthesis. $^1$H NMR (25° C., DMSO-$d_6$, ppm) δ7.41-7.82 (m, 17H), 6.79 (d, J=8.8 Hz, 2H), 6.25 (s, 1H), 5.93 (s, 1H), 1.99 (s, 3H). $^{13}$C NMR (25° C., DMSO-$d_6$, ppm) δ 168.8, 160.2, 152.6, 147.3, 142.9, 141.2, 137.1, 135.9, 134.8, 132.5, 131.8, 131.5, 128.7, 128.3, 125.9, 125.6, 124.8, 122.2, 121.5, 119.1, 114.9, 18.3. $^{19}$F NMR (25° C., DMSO-$d_6$, ppm, ext. CF$_3$COOH): δ −77.8 to −78.6. Anal. Calcd for $C_{29}H_{24}F_3NO_6S_3$: C, 54.79; H, 3.81; N, 2.20. Found: C, 55.09; H, 4.13; N, 1.88.

EXAMPLE 3

Synthesis of a Photoacid Generator of Formula (II)

Figure 21:
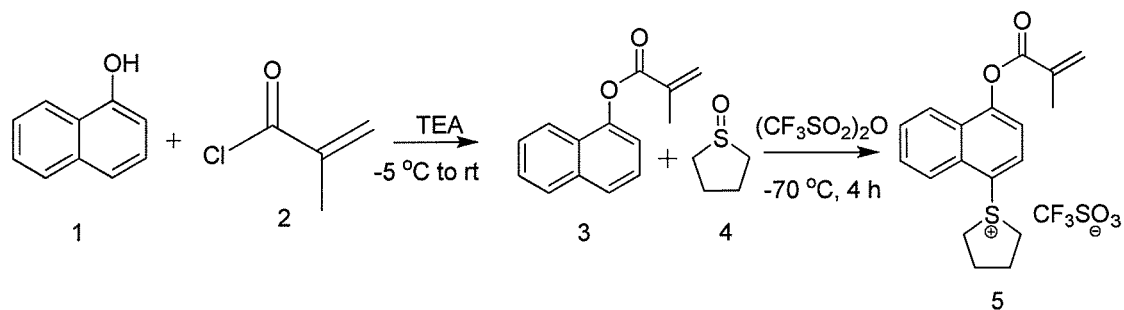
FIG. 21 illustrates a synthetic scheme for producing a photoacid generator of Formula (II) according to one embodiment of the present invention.

The following synthesis of a photoacid generator of Formula (II) is further illustrated in FIG. 21.

Synthesis of naphthalen-1-yl methacrylate (3)

An oven dried 250 mL 2 neck round bottom flask fitted with a dropping funnel and guard tube under inert atmosphere was charged with 100 mL of dry dichloromethane, 1-naphthol (1) (5.0 g, 34.6 mmol) and triethyl amine (7.0 g, 70.0 mmol). The flask was cooled to −5° C. (ice & water bath), methacryloyl chloride (2) (5.4 g, 52.0 mmol) was added slowly over a period of 15 min at −5° C. The reaction was stirred for 2 h at −5° C. and allow to warm to room temperature and stirred for another 2 h at room temperature. Reaction was monitored by TLC (until naphthol was absent). Reaction mixture was poured into a 500 mL separating funnel and the organic layer was washed with water and aq. Na$_2$CO$_3$ The organic layer were again washed with water and dried over anhydrous Na$_2$SO$_4$. DCM was removed under reduced pressure and the product was a viscous oil (compound 3) (6.61 g, yield 90%).

$^1$H NMR (25° C., CDCl$_3$, ppm) δ 7.80-8.0 (m, 2H), 7.60-7.70 (d, 1H), 7.30-7.45 (m, 3H), 7.25 (d, 1H), 6.60 (s, 1H), 5.85 (s, 1H), 2.20 (s, 3H);

GC-MS (m/z): 212.0 (100%).

Synthesis of 1-(4-Methacryloyoxy) naphthalene-1-yl)tetrahydro-1H-thiophenium trifluoromethanesulfonate (5): (Cyclic Cationic Photoacid Generator of Formula (II)

An oven dried 250 mL 2 neck round bottom flask fitted with a dropping funnel and guard tube under inert atmosphere was charged with 100 mL of dry dichloromethane, naphthalen-1-yl methacrylate(3)(5.0 g, 23.5 mmol), tetramethylene sulfoxide (4) (2.7 g, 25.9 mmol). The flask was cooled to −70° C. (dry ice & acetone bath), and trifluoromethanesulfonic anhydride (6.6 g, 23.5 mmol) was added slowly over a period of 15 min at −70° C. The reaction was stirred for 4 h at −70° C. and the reaction was monitored by TLC (until naphthalen-1-yl methacrylate was absent). After completion of the reaction, the mixture was allow to warm to room temperature the reaction mixture was poured into a 500 mL separating funnel saturated with aq NaHCO$_3$. The organic layer was washed with water and dried over anhydrous Na$_2$SO$_4$. DCM was removed under reduced pressure and the product was isolated (compound 5) (8.98 g, yield 85%).

Characterized by:

FT-IR (neat), Cm$^{-1}$, 3094 (Naphthyl, C—H stretching); 1737 (carbonyl C=O stretching);

$^1$H NMR (25° C., CDCl$_3$, ppm) δ 8.25-8.27 (d, 1H), 7.93-8.02 (d d, 2H), 7.50-7.71 (d d, 2H), 7.48 (d, 1H), 6.43 (s, 1H), 5.85 (s, 1H), 4.16-4.31 (m, 2H). 3.66-3.70 (m, 2H), 2.48-2.51 (m, 4H). 1.98-2.07 (s, 3H).

$^{13}$C NMR (25° C., CDCl$_3$, ppm) 6164.82, 151.53, 134.83, 130.01, 129.08, 128.58, 128.51, 127.74, 122.83, 122.49, 119.08, 47.88, 29.03, 18.28;

$^{19}$F NMR (25° C., ppm, CDCl$_3$, CF$_3$SO$_3$) δ−78.10 (s, 3F); ESI-MS (m/z) 299.0 (cat ion) CF$_3$SO$_3$148.7 (anion);

Anal. Calcd for $C_{19}H_{19}F_3O_5S_2$: C, 50.89; H, 4.24; S, 14.28. Found: C, 50.62; H, 4.31; S, 14.22.

EXAMPLE 4

Synthesis of a Lithographic Resist Comprising a Photoacid Generator of Formula (I)

Terpolymer was prepared by free radical polymerization in sealed pressure vessels. Hydroxystrene (HOST), 2-ethyl-2-adamantyl-methacrylate (EAMA), PAG and 2,2'-azobisisobutyronitrile (AIBN) as a free radical initiator (5 mole % to the monomers) were dissolved in freshly distilled anhydrous tetrahydrofuran (THF) and acetonitrile. Polymerization was performed at 65° C. for 24 hrs. The polymer solutions were precipitated into a large amount of diethyl ether or petroleum ether and dried in vacuum.

Figure 16:
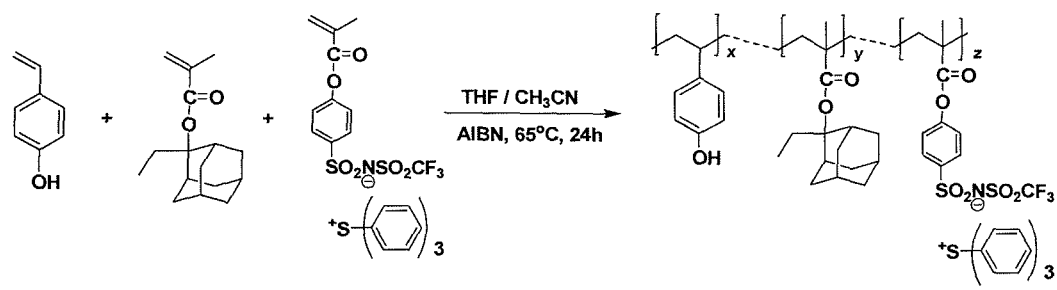
FIG. 16 illustrates a synthetic scheme for producing a lithographic resist according to one embodiment of the present invention.

The polymerization composition was calculated by $^1$H NMR. Table I provides molar feed ratios and other chemical and physical properties of the polymeric resist. FIG. 16 illustrates the foregoing synthesis.

TABLE I

| | Mole Feed Ratio | | | Polymer composition | | | Yield/ | Mw | Stability/ | Tg/ |
|---|---|---|---|---|---|---|---|---|---|---|
| Polymer | HOST | EAMA | PAG | HOST | EAMA | PAG | % | (PDI)[a] | °C.[b] | °C. |
| HS-EM-spPAG | 25 | 72.5 | 2.5 | 43.4 | 51.4 | 5.2 | 40.6 | 3100 (2.1) | 167 | 123 |

Lithographic Resist Properties

EXAMPLE 5

Acid Generation of Lithographic Resist Comprising a Photoacid Generator of Formula (I)

The following protocol was conducted for measuring acid generation. The lithographic resist of prepared in Example 4 was spin-cast onto a 4 inch Si wafer, whose weight was predetermined on an analytical balance, from 7.0 wt. % resist solutions in cyclohexanone. After casting, the resulting film was baked at 130° C. for 5 min to remove the solvent and were weighed again. The amount of resist on the film was calculated. The resist film was exposed to a 254 nm UV lamp equipped with a radiometer. Dose was calculated by exposure times multiplied by lamp intensity. The exposed film was stripped from the silicon wafer with DMSO and added to 1 mL of a stock solution of 0.3 mM tetrabromophenol blue (TBPB) in DMSO. The total volume was then raised to 10 mL by addition of DMSO. The resulting solution was characterized on a UV spectrometer. The amount of acid generated in the film by UV radiation was determined by monitoring the absorbance change of the TBPB indicator at 602 nm, against the calibration curves predetermined by using known amounts of triflic acid. Calibration curves showed a linear relationship between the amount of acid added to the indicator solution and the resulting absorbance intensity change at 602 nm. For comparison, the acid generation efficiency of the resist of Example 3 was expressed as mole of acid/mole of PAG units in the resist. The number of moles of PAG units in each resist was determined by $^1$H NMR and resist weight.

The lithographic resist of Example 3 demonstrates an acid generation efficiency of 89% according to the foregoing protocol.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. An anionic photoacid generator having the formula:

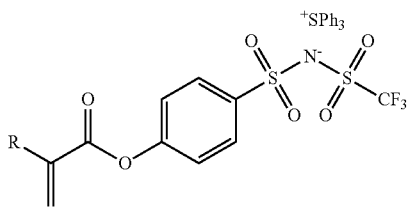

wherein R is selected from the group consisting of hydrogen, -alkyl and —NO$_2$.

2. An anionic photoacid generator having the formula:

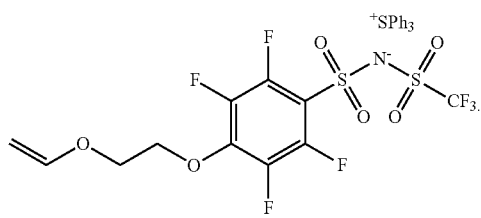 [SMILES: C=COCCOc1c(F)c(F)c(S(=O)(=O)[N-]S(=O)(=O)C(F)(F)F)c(F)c1F ; "+SPh3"]

3. An anionic photoacid generator having the formula:

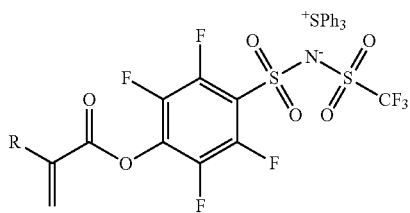

wherein R is selected from the group consisting of hydrogen, -alkyl and —NO$_2$.

4. A lithographic resist comprising a photoacid generator of Formula (I):

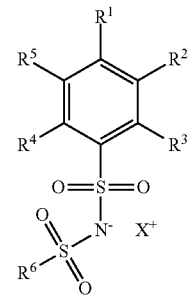

wherein $R^1$, $R^2$, $R^3$, $R^4$, $R^5$ and $R^6$ are independently selected from the group consisting of -hydrogen, -alkyl, -alkenyl, -alkynyl, -cycloalkyl, -fluoroalkyl, -fluoroalkenyl, fluoroalkynyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, -carboxyl, -hydroxyl, -halo, -cyano and -nitro, wherein the alkyl, alkenyl, alkynyl, cycloalkyl, aryl and heteroaryl groups of $R^1$-$R^6$ are optionally and independently substituted one of more times with a substituent selected from the group consisting of -alkyl, -alkenyl, -fluoroalkyl, -fluoroalkyl, -aryl, —O-alkyl, —O-alkenyl, —O-aryl, —O-alkylene-aryl, -carboxyl, -hydroxyl, -halo, and -nitro; and X+ is a compound selected from the group consisting of a sulfonium compound or an ionium compound,
or a photoacid generator of Formula (II):

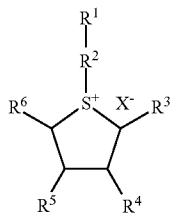

wherein
R¹ is selected from the group consisting of -hydrogen, -alkyl, -alkenyl, -alkynyl, -cycloalkyl, -aryl, -heteroaryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, —O-alkylene-O-alkenyl, and —OH;
R² is selected from the group consisting of alkylene, cycloalkylene, arylene, heteroarylene and polycyclic;
R³, R⁴, R⁵ and R⁶ are independently selected from the group consisting of -hydrogen, -alkyl, -alkenyl, -alkynyl, -cycloalkyl, -aryl, -heteroaryl, —O-alkyl, —O-alkenyl, —O-aryl, —O-heteroaryl, —O-alkylene-aryl, —O-alkylene-arylene-alkyl, —O-alkylene-arylene-alkenyl;
wherein the alkyl, alkenyl, alkynl, cycloalkyl, aryl, and heteroaryl of R¹ and R³-R⁶ are optionally and independently substituted one or more times with a substituent selected from the group consisting of -alkyl, -alkenyl, -alkynyl, cycloalkyl, -aryl, heteroaryl, —O-alkyl, —O-alkenyl, —O-aryl, —O-alkylene-aryl, -carboxyl, -hydroxyl, -halo, and -nitro; and
X⁻ is selected from the group consisting of $CF_3SO_3^-$, $C_4F_9SO_3$— and an anionic photoacid generator of Formula (I) wherein the counter cation is not present, or a combination of the photoacid generator of Formula (I) and the photoacid generator of Formula (II),
wherein the lithographic resist further comprises an energy harvesting unit and the energy harvesting unit comprises a conjugated polymer.

5. The lithographic resist of claim 4, wherein the conjugated polymer comprises polythiophenes, polyphenylene vinylene (PPV), poly(-vinylpyridine) (P2VP), polyamides, poly(N-vinylcarbazole) (PVCZ), polypyrrole (PPy), polyaniline (PAn).

* * * * *